United States Patent

Weber et al.

[11] 4,029,666
[45] June 14, 1977

[54] BENZENESULFONYL-UREAS AND PROCESS FOR PREPARING THEM

[75] Inventors: Helmut Weber, Frankfurt am Main; Walter Aumüller; Karl Muth, both of Kelkheim, Taunus; Rudi Weyer, Frankfurt am Main; Felix Helmut Schmidt, Mannheim, all of Germany

[73] Assignee: Hoechst Aktiengesellschaft, Frankfurt am Main, Germany

[22] Filed: Dec. 8, 1971

[21] Appl. No.: 206,190

Related U.S. Application Data

[63] Continuation-in-part of Ser. No. 750,005, Aug. 5, 1968, abandoned.

[30] Foreign Application Priority Data

Aug. 9, 1967 Germany .......................... 53180

[52] U.S. Cl. .................. 260/293.73; 260/293.54; 260/293.68; 260/239 BF; 260/326.1; 424/244; 424/267; 424/274; 424/275

[51] Int. Cl.² .................................. C07D 211/06

[58] Field of Search ... 260/553 DA, 553 D, 293.54, 260/293.68, 293.75, 239 BF, 326.1

[56] References Cited

UNITED STATES PATENTS 3,445,470   5/1969   Jucker et al. ............. 260/553 D X

FOREIGN PATENTS OR APPLICATIONS 684,654   7/1966   Belgium ................ 260/553 DA
719,277   2/1969   Belgium ................ 260/553 DA Primary Examiner—Gerald A. Schwartz
Attorney, Agent, or Firm—Curtis, Morris & Safford

[57] ABSTRACT

Benzenesulfonyl-ureas of the formula

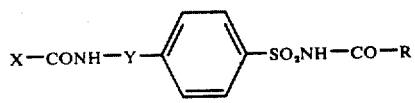

wherein
X represents a)

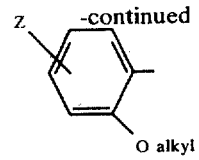

in which Z represents hydrogen, halogen, a trifluormethyl group, an alkyl or an alkoxyl radical in 4- or 5-position, or

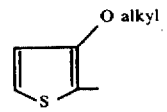

Y represents $-CH_2-CH_2-$, $-CH-(CH_3)-CH_2-$ or $-CH_2-CH-(CH_3)-$, R represents a radical of
a. pentamethylene-imine, which may be substituted by 1 to 3 methyl group or by an endoalkylene group of 1 to 3 carbon atoms,
b. hexamethylene-imine, which may be substituted by an endoethylene group in β-ε-position,
c. heptamethylene-imine,
d. hexahydro-isoindoline, tetrahydro-isoindoline, 4,7-endoalkylene-hexahydro-, 4,7-endoalkylene-tetrahydro-isoindoline, the endoalkylene group of which may contain 1 - 2 carbon atoms and the double linkage of the tetrahydro group being in 5,6-position,
e. N-3-azaspiro-[5,5]-undecane,
f. the groups

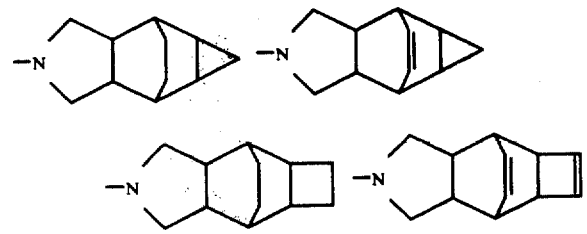

and their pharmaceutically acceptable alkali- or alkaline earth-metal salts.

4 Claims, No Drawings

BENZENESULFONYL-UREAS AND PROCESS FOR PREPARING THEM

The present application is a continuation-in-part of U.S. patent application Ser. No. 750,005 filed Aug. 5, 1968 and now abandoned.

The present invention is concerned with new benzenesulfonyl-ureas and with their manufacture and use, it provides benzenesulfonyl-ureas of the formula

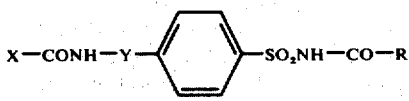

and their physiologically tolerable salts. The new benzenesulfonyl-ureas, in the free form or in the form of their physiologically tolerable salts, have blood sugar lowering properties and are distinguished by a strong and long lasting hypoglycemic action.

In the above formula
X represents

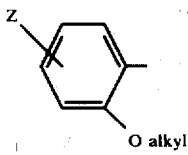

in which Z represents hydrogen, halogen, a trifluormethyl group, an alkyl or an alkoxyl radical in 4- or 5-position,

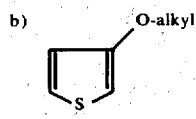

Y represents $-CH_2-CH_2-$, $-CH-(CH_3)-CH_2-$ or $-CH_2-CH-(CH_3)-$,

R represents a radical of
a. pentamethylene-imine, which may be substituted by 1 to 3 methyl groups or by an endoalkylene group of 1 to 3 carbon atoms,
b. hexamethylene-imine, which may be substituted by an endoethylene group in β-ε-position,
c. heptamethylene-imine,
d. hexahydro-isoindoline, tetrahydro-isoindoline, 4,7-endoalkylene-hexahydro-, 4,7-endoalkylene-tetrahydroisoindoline, the endoalkylene group of which may contain 1 – 2 carbon atoms and the double linkage of the tetrahydro group being in 5,6-position,
e. N-3-azaspiro-[5,5]-undecane,
f. the groups

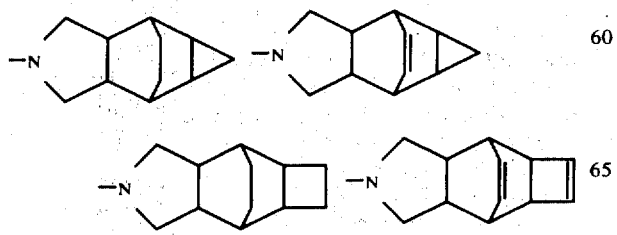

The term "alkyl" used throughout the specification is intended to mean alkyl groups containing 1 to 4 carbon atoms, in a straight or branched chain.

As the part X in the above formula, there enter into consideration the following ring systems:

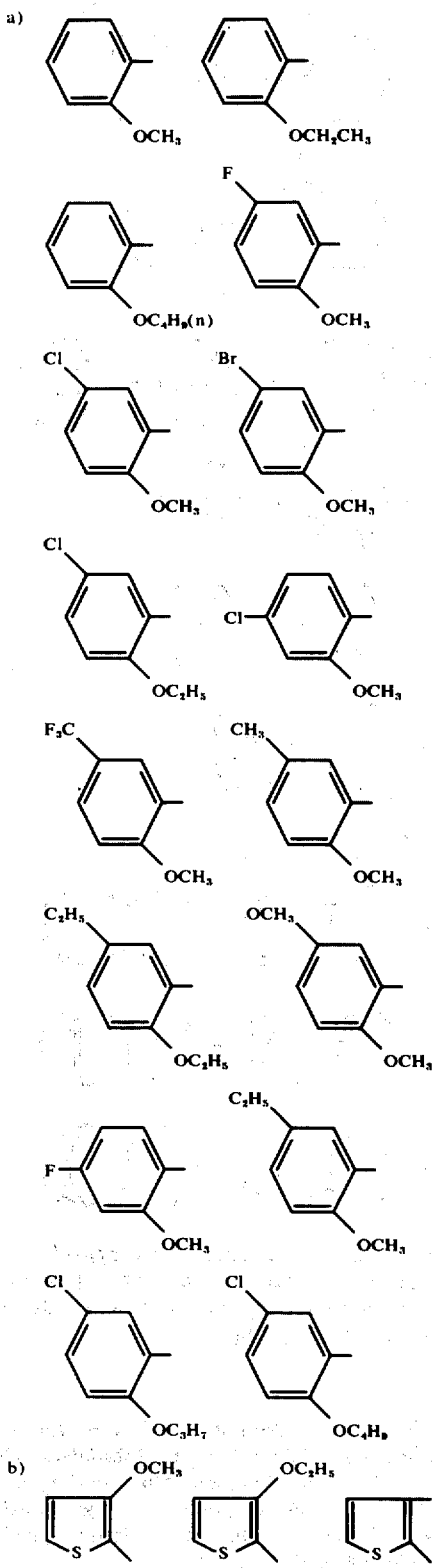

As the part R, there may be mentioned:

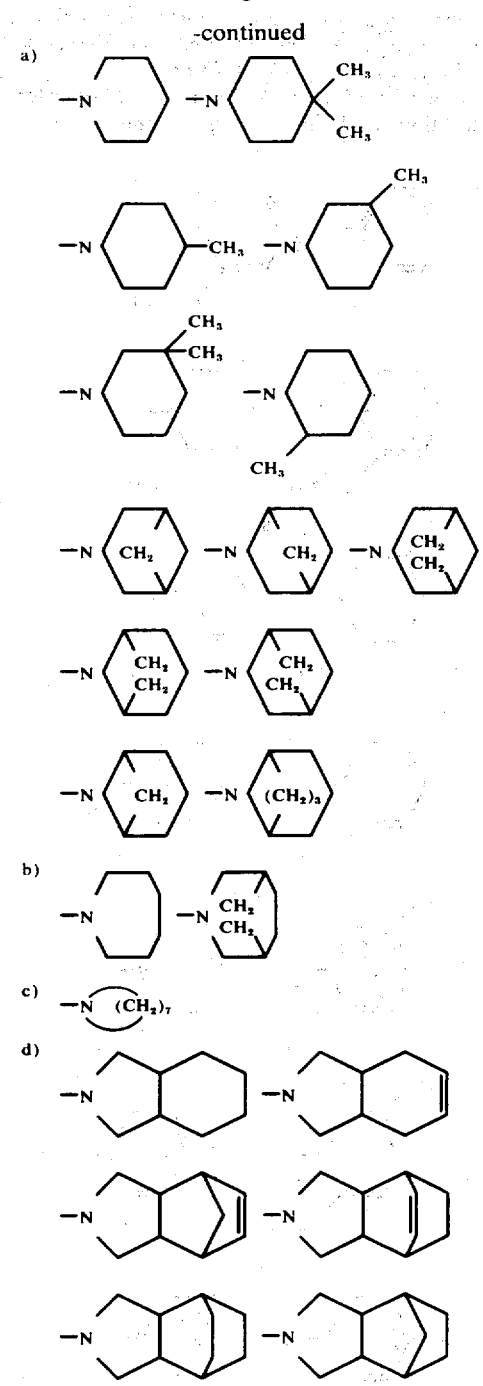

The present invention furthermore provides a process for preparing the new benzenesulfonyl-ureas, wherein benzenesulfonylcarbamic acid esters which are substituted by the group

X—CO—NH—Y— are reacted with amines of the formula RH or with their salts, and, if desired, the compounds obtained are converted into salts by treatment with alcaline agents.

The benzenesulfonyl-carbamic acid esters mentioned may contain a low molecular alkyl group or a phenyl group in the alcohol component.

With regard to reaction conditions, the manner of carrying out the process of the present invention may, in general, be varied within wide limits and adapted to each individual case. For example, the reactions may be carried out in inert solvents such as dioxane or toluene, at temperatures in the range of from 80° to 110° C and at different pH-values (by using salts of the amines RH). It has proved to be advantageous to use the amine or the salts thereof in an excess.

The blood sugar lowering action of the benzenesulfonylureas of the present invention was ascertained by administering them, for example in form of the sodium salt, to normally fed rabbits in doses of 10 mg/kg and determining the blood sugar value according to the known method of Hagedorn-Jensen or by means of an autoanalyser for a prolonged period of time.

Thus, we have found, for example, that 10 mg/kg of N-[4-($\beta$-<2-methoxy-5-bromobenzamido>-ethyl)-benzenesulfonyl]-N',N'-(3,3-dimethyl-pentamethylene)-urea provoke after 3 hours a lowering of the blood sugar of 23%, which after 24 hours still amounts to 24% and receds to zero only after 48 hours, whereas the known N-[4-methyl-benzenesulfonyl]-N'-butyl-urea has no blood sugar lowering effect when administered to rabbits in a dose of less than 25 mg/kg.

The strong hypoglycemic action of the described benzenesulfonyl-ureas becomes more evident when the dose is further reduced. When N-[4-($\beta$-<2-methoxy-5-bromobenzamido>-ethyl)-benzenesulfonyl]-N',N'-(3,3-dimethyl-pentamethylene)-urea is administered to rabbits in dose of 0.2 mg/kg and N-[4-($\beta$-<2-methoxy-5-chlorobenzamido>-ethyl)-benzenesulfonyl]-N',N'-(3,3-dimethyl-pentamethylene)-urea is administered in a dose of 0.2 mg/kg to rabbits, a distinct lowering of the blood sugar can still be observed.

With regard to toxicity of the compounds, there have been determined values which are of the same order as those of such benzenesulfonyl-ureas as the N-[4-methyl-benzenesulfonyl]-N'-n-butyl-urea and the N-[4-methyl-benzenesulfonyl]-N'-cyclohexyl-urea, the $LD_{50}$ p.o. of which are 2.5 and 4.8 g/kg, respectively.

Hence, the products of the present invention have a very strong blood sugar lowering action and are extraordinarily well tolerated.

The benzenesulfonyl-ureas of the present invention are preferably used for the manufacture of orally administrable pharmaceutical preparations having blood sugar lowering action for the treatment of diabetes mellitus and may be used as such or in the form of their physiologically tolerable salts or in the presence of substances which cause such salt formation. The salts are the ones commonly used in the pharmaceutical industry to force physiologically tolerable salts. For the formation of salts, there may be used, for example, alkaline agents such as alkali metal hydroxides or alkaline earth metal hydroxides or alkali metal or alkaline earth metal carbonates or bicarbonates.

The present invention, therefore, also provides pharmaceutical preparations which comprise a benzenesulfonyl-urea of the above general formula or a physiologically tolerated salt thereof, in admixture or conjunction with a pharmaceutically suitable carrier.

The pharmaceutical preparations are advantageously in the form of tablets and the pharmaceutically suitable carrier may be, for example talc, starch, lactose, tragacanth or magnesium stearate.

A pharmaceutical preparation, for example a tablet or a powder, containing a benzenesulfonyl-urea of the invention or a physiologically tolerated salt thereof as the active substance, with or without one of the aforementioned carriers, is advantageously brought into a suitable dosage unit form. The dose chosen should comply with the activity of the benzenesulfonyl-urea or of the physiologically tolerated salt thereof used and the desired effect. Advantageously, the dose per unit amounts to about 0.5 to 100 mg, preferably 2 to 10 mg, but considerably higher or lower dosage units may also be used, which, if desired, are divided or multiplied prior to their administration.

The following examples illustrate the invention but they are not intended to limit it thereto:

EXAMPLE 1:

N-[4-(β-<2-Methoxy-5-methyl-benzamido>-ethyl)-benzenesulfonyl]-N',N'-(3-methyl-pentamethylene)-urea 4 g of N-[4-(β-<2-methoxy-5-methyl-benzamido>-ethyl)-benzenesulfonyl]-methyl-urethane (melting point 175° – 177° C) were suspended in 75 ml of dioxane and, after addition of 1.1 g of 4-methyl-piperidine, the whole was heated for 15 minutes to 110° C. Then, again 1.1 g of 4-methyl-piperidine was added, the whole was heated for one hour under reflux and, after cooling, it was combined with water. The N-[4-(β-<2-methoxy-5-methyl-benzamido>-ethyl)-benzenesulfonyl]-N',N'-(3-methyl-pentamethylene)-urea that had precipitated was purified by dissolution and repeated crystallization in a mixture of ammonia and hydrochloric acid and by recrystallization from methanol (melting point 167° – 169° C).

In analogous manner there were obtained:
from N-[4-(β-<2-methoxy-5-chlorobenzamido>-ethyl)-benzenesulfonyl]-methyl-urethane (melting point 189° – 191° C):
the N-[4-(β-<2-methoxy-5-chlorobenzamido>-ethyl)-benzenesulfonyl]-N',N'-pentamethylene-urea, melting point 184° – 186° C (from methanol); and
the N-[4-(β-<2-methoxy-5-chlorobenzamido>-ethyl)-benzenesulfonyl]-N',N'-(2-methyl-pentamethylene)-urea, melting point 150° – 152° C (from methanol);
from N-[4-(β-<2-methoxy-benzamido>-ethyl)-benzenesulfonyl]-methyl-urethane (melting point 174° – 176° C):
the N-[4-(β-<2-methoxy-benzamido>-ethyl)-benzenesulfonyl]-N',N'-(3-methyl-pentamethylene)-urea, melting point 149° – 151° C (from methanol);
from N-[4-(β-<2-methoxy-4-chlorobenzamido>-ethyl)-benzenesulfonyl]-methyl-urethane melting point 178° – 180° C):
the N-[4-(β-<2-methoxy-4-chlorobenzamido>-ethyl)-benzenesulfonyl]-N',N'-(3-methyl-pentamethylene)-urea, melting point 194° – 196° C (from methanol);
from N-[4-(β-<2-methoxy-5-bromobenzamido>-ethyl)-benzenesulfonyl]-methyl-urethane (melting point 197° – 199° C):
the N-[4-(β-<2-methoxy-5-bromobenzamido>-ethyl)-benzenesulfonyl]-N',N'-(3,3-dimethyl-pentamethylene)-urea, melting point 143° C (from ethylacetate);
from N-[4-(β-<2-methoxy-5-chlorobenzamido>-ethyl)-benzenesulfonyl]-methyl-urethane (melting point 189° – 191° C):

the N-[4-(β-<2-methoxy-5-chlorobenzamido>-ethyl)-benzenesulfonyl]-N',N'-hexamethylene-urea, melting point 100° – 102° C (from methanol);
the N-[4-(β-<2-methoxy-5-chlorobenzamido>-ethyl)-benzenesulfonyl]-4,7-endomethylene-hexahydro-isoindolinyl-carboxamide, melting point 193° – 195° C (from methanol) and
the N-[4-(β-<2-methoxy-5-chlorobenzamido>-ethyl)-benzenesulfonyl]-4,7-endomethylene Δ5,6-tetrahydro-isoindolinyl-2-carboxamide, melting point 191° – 193° C (from methanol/dioxane);
from N-[4-(β-<2-methoxy-benzamido>-ethyl)-benzenesulfonyl]-methyl-urethane (melting point 174° – 176° C):
the N-[4-(β-<2-methoxy-benzamido>-ethyl)-benzenesulfonyl]-N',N'-hexamethylene-urea, melting point 168° – 170° C (from methanol);
from N-[4-(β-<2-methoxy-5-chlorobenzamido>-ethyl)-benzenesulfonyl]-methyl-urethane (melting point 189° – 191° C):
the N-[4-(β-<2-methoxy-5-chlorobenzamido>-ethyl)-benzenesulfonyl]-N',N'-(3-methyl-pentamethylene)-urea, melting point 172° – 174° C (dissolved and reprecipitated from a mixture of sodium carbonate and hydrochloric acid);
the N-[4-(β-<2-methoxy-5-chlorobenzamido>-ethyl)-benzenesulfonyl]-Δ5-tetrahydro-isoindolino-2-carboxamide, melting point 161° – 163° C;
the N-[4-(β-<2-methoxy-5-chlorobenzamido>-ethyl)-benzenesulfonyl]-hexahydro-isoindolino-2-carboxamide, melting point 189° – 190.5° C;
the N-[4-(β-<2-methoxy-5-chlorobenzamido>-ethyl)-benzenesulfonyl]-N',N'-(3,3-dimethyl-pentamethylene)-urea, melting point 145° C (dissolved and reprecipitated from a mixture of sodium carbonate and hydrochloric acid);
the N-[4-(β-<2-methoxy-5-chlorobenzamido>-ethyl)-benzenesulfonyl]-N',N'-(1,5-endoethylene-pentamethylene)-urea, melting point 195° – 196° C (from a mixture of dimethylformamide, methanol and water);
the N-[4-(β-<2-methoxy-5-chlorobenzamido>-ethyl)-benzenesulfonyl]-N',N'-(1,4-endoethylene-pentamethylene)-urea, melting point 178° – 180° C (purified via ammonia) and
the N-[4-(β-<2-methoxy-5-chlorobenzamido>-ethyl)-benzenesulfonyl]-N',N'-(1,5-endopropylene-pentamethylene)-urea, melting point 152° – 153° C (from dimethylfromamide/methanol/water);
from N-[4-(β-<2-methoxy-5-methylbenzamido>-ethyl)-benzenesulfonyl]-methyl-urethane (melting point 175° – 177° C):
the N-[4-(β-<2-methoxy-5-methylbenzamido>-ethyl)-benzenesulfonyl]-N',N'-(3,3-dimethyl-pentamethylene)-urea, melting point 132° C (purified via the Sodium Salt).

In analogous manner, there was obtained
from N-[4-(β-<3-methoxythiophen-2-carbonamido)-ethyl)-benzenesulfonyl]-methyl-urethane (melting point 226° – 228° C);
from N-[4-(β-<3-methoxy-thiophen-2-carbonamido>-ethyl)-benzenesulfonyl]-methyl-urethane (melting point 226° – 228° C):
the N-[4-(β-<3-methoxy-thiophen-2-carbonamido>-ethyl)-benzenesulfonyl]-N',N'-(3- methyl-pentamethylene)-urea, melting point 215° – 217° C (from methanol, dimethylformamide);

from N-[4-(β-<2-ethoxybenzamido>-ethyl)-benzenesulfonyl]-methyl-urethane (melting point 172° – 174° C):

the N-[4-(β-<2-ethoxy-benzamido>-ethyl)-benzenesulfonyl]-N',N'-(3-methyl-pentamethylene)-urea, melting point 156° – 158° C (from methanol);

from N-[4-(β-<2-methoxy-ethoxy-benzamido>-ethyl)-benzenesulfonyl]-methyl-urethane (melting point 123° – 125° C):

the N-[4-(β-<2-methoxy-ethoxy-benzamido>-ethyl)-benzenesulfonyl]-N',N'-(3-methyl-pentamethylene)-urea, melting point 112° – 113° C (decomposition) (from methanol);

from N-[4-(β-<2-ethoxy-5-fluorobenzamido>-ethyl)-benzenesulfonyl]-methyl-urethane (melting point 193° – 195° C):

the N-[4-(β-<2-ethoxy-5-fluoro-benzamido>-ethyl)-benzenesulfonyl]-N',N'-(3-methyl-pentamethylene)-urea, melting point 178° – 179° C (from methanol);

from N-[4-(β-<2-methoxy-5-methyl-benzamido>-ethyl)-benzenesulfonyl]-methyl-urethane (melting point 175° – 177° C):

the N-[4-(β-<2-methoxy-5-methyl-benzamido>-ethyl)-benzenesulfonyl]-N',N'-(2-methyl-pentamethylene)-urea, melting point 156° – 158° C (from methanol);

from N-[4-(β-<2-methoxy-5-trifluoro-methyl-benzamido>-ethyl)-benzenesulfonyl]-methyl-urethane (melting point 179° – 181° C:

the N-[4-(β-<2-methoxy-5-trifluoro-methyl-benzamido>-ethyl)-benzenesulfonyl]-N',N'-(3-methyl-pentamethylene)-urea, melting point 158° – 160° C (from methanol);

from N-[4-(β-<2-methoxy-5-chlorobenzamido>-ethyl)-benzenesulfonyl]-methyl-urethane (melting point 178° – 179° C):

the N-[4-(β-<2-methoxy-5-chlorobenzamido>-ethyl)-benzenesulfonyl-amino-carbonyl]-3-azaspiro-[5,5]-undecane, melting point 125° C;

from N-[4-(β-<2-methoxy-5-methyl-benzamido>-ethyl)-benzenesulfonyl]-ethyl-urethane (melting point 166° – 170° C):

the N-[4-(β-<2-methoxy-5-methyl-benzamido>-ethyl)-benzenesulfonyl-amino-carbonyl]-3-azaspiro-[5,5]-undecane, melting point 110° C (decomposition);

from N-[4-(β-<2-methoxy-5-fluoro-benzamido>-ethyl)-benzenesulfonyl]-ethyl-urethane (melting point 123° C):

the N-[4-(β-<2-methoxy-5-fluoro-benzamido>-ethyl)-benzenesulfonyl-amino-carbonyl]-3-azaspiro-[5,5]-undecane, melting point 151° – 153° C;

from N-[4-(β-<2-methoxy-benzamido>-ethyl)-benzenesulfonyl]-ethyl-urethane (melting point 144° C):

the N-[4-(β-<2-methoxy-benzamido>-ethyl)-benzenesulfonyl-amino-carbonyl]-3-azaspiro-[5,5]-undecane, melting point 166° – 168° C.

EXAMPLE 2:

N-[4-(β-<5-chloro-2-methoxy-benzamido>-ethyl)-benzenesulfonyl-amino-carbonyl]-4,7-endocyclopropylene-Δ5-hexahydroisoindol 10.7 g of N-[4-(β-<5-chloro-2-methoxy-benzamido>-ethyl)-benzenesulfonyl]-methyl-urethane were dissolved in 100 ml of dioxane and, after addition of 4.08 g of 4,7-endo-cyclopropylene-Δ5-hexahydroisoindol, the whole was heated for 1½ hour under reflux to the boiling temperature. The dioxane was removed by distillation under reduced pressure. The N-[4-(β-<5-chloro-2-methoxy-benzamido>-ethyl)-benzenesulfonyl-amino-carbonyl]-4,7-endocyclopropylene-Δ5-hexahydroisoindol thus obtained was found to melt, after recrystallization from a mixture of ethyl acetate and dioxane, at 179° – 181° C.

In analogous manner, there was obtained from the mentioned sulfonyl-urethane and 4,7-endocyclopropylene-octahydroisoindol:

the N-[4-(β-<5-chloro-2-methoxy-benzamido>-ethyl)-benzenesulfonyl-amino-carbonyl]-4,7-endocyclopropylene-octahydroisoindol, melting point 186° – 188° C;

from the mentioned sulfonyl-urethane and 4,7-endocyclobutylene-octahydroisoindol:

the N-[4-(β-<5-chloro-2-methoxy-benzamido>-ethyl)-benzenesulfonyl-amino-carbonyl]-4,7-endocyclobutylene-octahydro-isoindol, melting point 175° – 176° C (from dioxane).

In an analogous manner there were obtained:

N-[4-(β-<2-methoxy-5-methyl-benzamido>-ethyl)-benzenesulfonyl-amino-carbonyl]-4,7-enodcyclobutenylene-Δ5-hexahydroisoindol melting point 125° – 127° C (decomposition from ethyl acetate)

N-[4-(β-<2-methoxy-5-chloro-benzamido>-ethyl)-benzenesulfonyl-amino-carbonyl]-4,7-endocyclobutenylene-Δ5-hexahydroisoindol melting point 130° C (decomposition)

N-[4-(β-<2-methoxy-benzamido>-ethyl)-benzenesulfonyl-amino-carbonyl]-4,7-endocyclobutenylene-Δ5-hexahydroisoindol melting point 210° – 212° (from ethyl acetate-dioxane)

N-[4-(β-<5-methyl-2-methoxy-benzamido>-ethyl)-benzenesulfonyl-aminocarbonyl]-N'-4,7-endo-cyclopropylene-Δ5-hexahydroisoindol melting point 169° – 171° (from methanol)

N-[4-(β-<2-methoxy-benzamido>-ethyl)-benzenesulfonyl-amino-carbonyl]-4,7-endo-cyclobutylene-octahydroisoindol melting point 223° – 225° (from ethyl acetate)

N-[4-(β-<2-methoxy-5-methyl-benzamido>-ethyl)-benzenesulfonyl-amino-carbonyl]-4,7-endo-cyclobutylene-octahydroisoindol melting point 182° – 184° (from ethyl acetate-dioxane)

N-[4-(β-<2-methoxy-5-bromo-benzamido>-ethyl)-benzenesulfonyl- amino-carbonyl]-4,7-endo-cyclobutylene-octahydroisoindol melting point 204° – 206° (from ethyl acetate)

N-[4-(β-<2,5-dimethoxy-benzamido>-α-methylethyl)-benzenesulfonyl]-N',N'-hexamethylene-urea, melting point 181°–183° C N-[4-(β-<2,5-dimethoxy-benzamido>-α-methylethyl)-benzenesulfonyl-aminocarbonyl]-4,7-endocyclobutylene-Δ5-hexahydroisoindol, melting point 185°–187° C N-[4-(β-<2-methoxy-5-chloro-benzamido>-propyl)-benzenesulfonyl]-N',N'-heptamethylene-urea, melting point 201° C N-[4-(β-<2-methoxy-5-bromo-benzamido>-ethyl)-benzenesulfonyl-aminocarbonyl]-4,7-endoethylene-octahydro-isoindol, melting point 189°–191° C.

N-[4-(β-<2-methoxybenzamido>-ethyl)-benzenesulfonyl-amino-carbonyl]-4,7-endoethylene-octahydro-isoindol, melting point 191°–192° C N-[4-(β-<2-methoxy-5-methylbenzamido>-ethyl)-benzenesulfonyl-amino-carbonyl]-4,7-endoethylene-octahydro-isoindol, melting point 192°–194° C N-[4-(β-<2-methoxy-5-chloro-benzamido>-ethyl)-benzenesulfonyl-amino-carbonyl]-4,7-endoethylene-octahydro-isoindol, melting point 171°–173° C N-[4-(β-<2-methoxy-5-methyl-benzamido>-ethyl)-benzenesulfonyl-amino-carbonyl]-4,7-endomethylene-octahydro-isoindol, melting point 207°–209° C N-[4-(β-<3-ethoxy-thiophen-2-carbamido>-ethyl-benzenesulfonyl-amino-carbonyl]-4,7-endomethylene-octahydro-isoindol, melting point 182°–184° C N-[4-(β-<2-methoxy-5-bromo-benzamido>-ethyl)-benzenesulfonyl-amino-carbonyl]-4,7-endomethylene-Δ⁵-hexahydroisoindol, melting point 141°–143° C N-[4-(β-<2-methoxy-5-methyl-benzamido>-ethyl)-benzenesulfonyl-amino-carbonyl]-4,7-endomethylene-Δ⁵-hexahydroisoindol, melting point 166°–168° C.

We claim:
1. Benezenesulfonyl-urea of the formula

wherein X is 2-methoxy-5-chlorophenyl, Y is —CH$_2$CH$_2$— and R is N,N-3,3-dimethyl-pentamethylene.

2. Benezenesulfonyl-urea of the formula

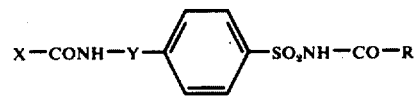

wherein X is 2-methoxy-5-chlorophenyl, Y is —CH$_2$CH$_2$— and R is N,N-3-methylpentamethylene.

3. Benezenesulfonyl-urea of the formula

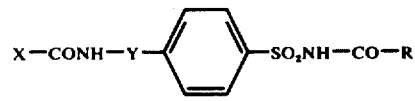

wherein X is 2-methoxy-5-methylphenyl, Y is —CH$_2$CH$_2$— and R is N,N-3,3-dimethylpentamethylene.

4. Benezenesulfonyl-urea of the formula

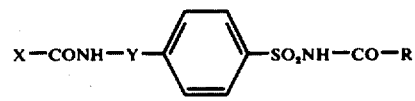

wherein X is 3-methoxy-5-chlorophenyl, Y is —CH$_2$CH$_2$— and R is N,N-hexamethylene.

* * * * *